US006397843B1

United States Patent
Tien-Tsai (10) Patent No.: US 6,397,843 B1
(45) Date of Patent: Jun. 4, 2002

(54) ELECTRICAL AND MANUAL PRESSING DEVICE OF AUTOMATED AIR BLOWING FOR FIRST-AID CARDIOPULMONARY RESUSCITATION

(76) Inventor: Chang Tien-Tsai, 5F, 28 Kuo-Hsiao Road, Hsin-Tien City, Taipei Hsien (TW)

( * ) Notice: Subject to any disclaimer, the term of this patent is extended or adjusted under 35 U.S.C. 154(b) by 0 days.

(21) Appl. No.: 09/505,996

(22) Filed: Feb. 17, 2000

(30) Foreign Application Priority Data

Jan. 21, 2000 (TW) .................................... 89101047 A (51) Int. Cl.⁷ ............................................. A61M 16/00
(52) U.S. Cl. ........................... 128/204.18; 128/205.18; 600/16
(58) Field of Search .......... 128/204.18, 205.13–205.19, 128/202.28, 200.24, 206.29, 909, 202.29, 203.11; 600/16; 601/41, 44, 133, 134, 135

(56) References Cited

U.S. PATENT DOCUMENTS

| | | | | |
|---|---|---|---|---|
| 2,902,992 A | * | 9/1959 | Renvall | 128/29 |
| 3,336,920 A | * | 8/1967 | Thomas | 128/53 |
| 3,348,536 A | * | 10/1967 | Tambascia | 128/53 |
| 3,509,899 A | * | 5/1970 | Hewson | 128/205.13 |
| 3,552,390 A | * | 1/1971 | Muller | 128/145.6 |
| 4,198,963 A | * | 4/1980 | Barkalow et al. | 128/53 |
| 4,297,999 A | * | 11/1981 | Kitrell | 128/205.16 |
| 4,326,507 A | * | 4/1982 | Barkalow | 128/54 |
| 4,349,015 A | * | 9/1982 | Alferness | 128/205.13 |
| 4,424,806 A | * | 1/1984 | Newman et al. | 128/205.25 |
| 4,452,241 A | * | 6/1984 | Sarnoff et al. | 128/204.18 |
| 5,109,833 A | * | 5/1992 | Frimberger | 128/205.13 |
| 5,327,887 A | * | 7/1994 | Nowakowski | 128/204.21 |
| 5,345,929 A | * | 9/1994 | Jansson et al. | 12/205.13 |
| 5,490,820 A | * | 2/1996 | Schock et al. | 601/41 |
| 5,657,751 A | * | 8/1997 | Karr, Jr. | 128/205.18 |
| 5,743,864 A | * | 4/1998 | Baldwin, II | 601/41 |
| 5,769,800 A | * | 6/1998 | Gelfand et al. | 60/151 |
| 5,772,613 A | * | 6/1998 | Gelfand et al. | 601/41 |
| 5,787,880 A | * | 8/1998 | Swanson et al. | 128/202.28 |
| 5,823,185 A | * | 10/1998 | Chang | 128/204.18 |
| RE36,460 E | * | 12/1999 | Klatz et al. | 604/26 |
| 6,234,984 B1 | * | 5/2001 | Kelly et al. | 601/41 |

* cited by examiner

*Primary Examiner*—John G. Weiss
*Assistant Examiner*—Teena Mitchell
(74) *Attorney, Agent, or Firm*—Troxell Law Office PLLC (57) ABSTRACT

An electrical and manual pressing device of automatic air blowing for first-aid cardiopulmonary resuscitation comprises pressing unit, an air storage tank, a control chamber, air levels, and a sucking disk. The device has the following functions: filling the air by way of electrical actuation or manual pressing, offering a great deal of air, maintaining a constant pressing force against the heart, quickly fixing the sucking disk at a proper pressing position based on the size of the bust line, checking a breathing reaction of the patient by way of the air level, checking the heart beat by way of the stethoscope, offering oxygen or the fresh air after the heat beat restoring by way of the pumping ball.

12 Claims, 11 Drawing Sheets

FIG. 1

(Prior art)

ELECTRICAL AND MANUAL PRESSING DEVICE OF AUTOMATED AIR BLOWING FOR FIRST-AID CARDIOPULMONARY RESUSCITATION

BACKGROUND OF THE INVENTION

1. Field of the Invention

The present invention relates to a device of first-aid air blowing for cardiopulmonary resuscitation, and particularly to an automatic device of first-aid air blowing for cardiopulmonary resuscitation, which can be operated electrically and manually.

2. Description of Related Art

Figure 1:
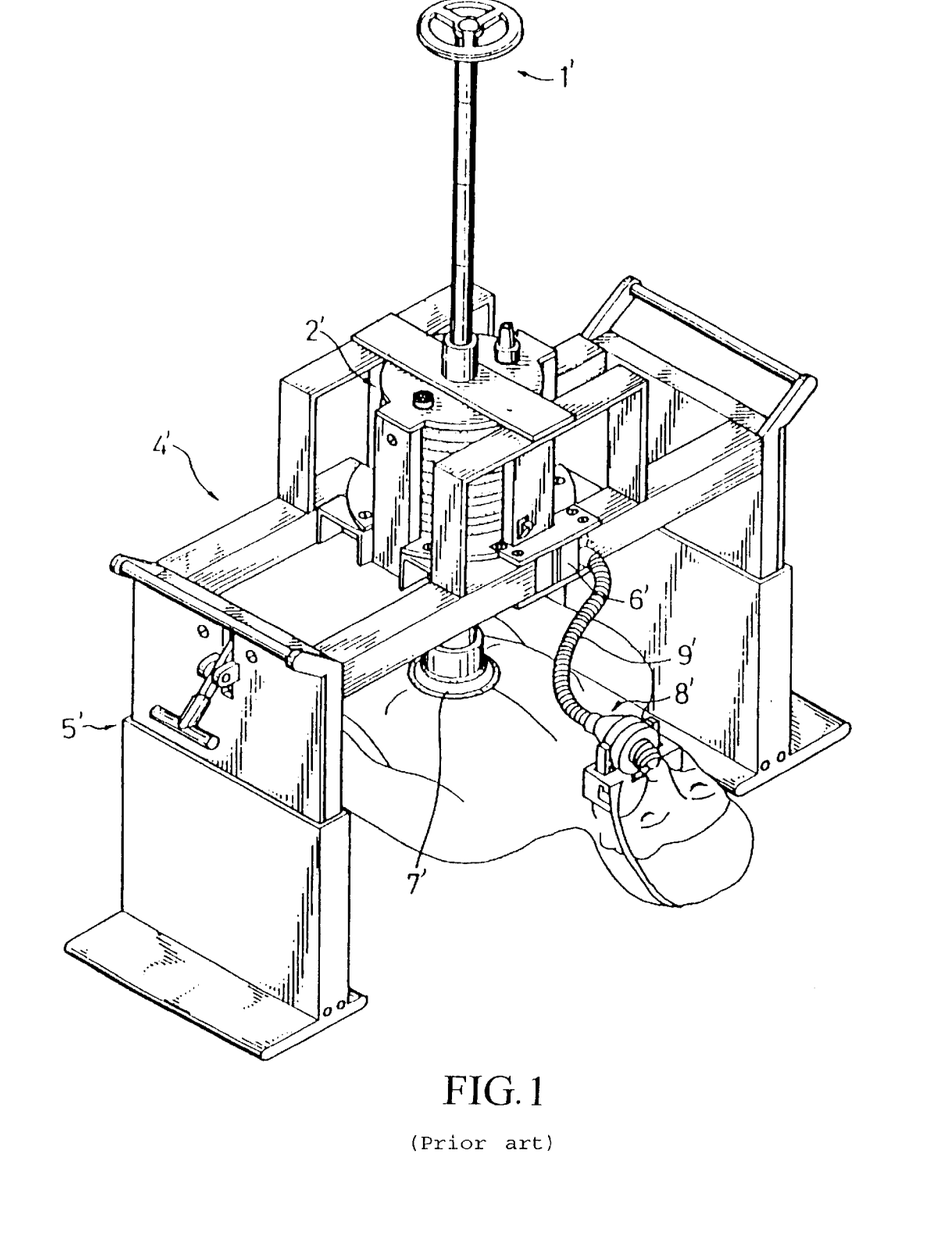
FIG. 1 (Prior art) is a perspective view of the cardiopulmonary resuscitation first-aid device disclosed in U. S. Pat. No. 5,823,185.

The present inventor has disclosed a manual Pressing and automatic Air Breathing Cardiopulmonary Resuscitation First-aid Device in U.S. Pat. No. 5,823,185. As shown in FIG. 1, the device comprises a manual pressing shaft 1', a pump 2', an air storage tank (under the pump 2'), a frame 4', a height-adjustable stand 5', an air control valve 6', a sucking disk 7', a mouth-nose breather 8', and an air passage pipe 9'. In order to revive a patient quickly, the device of said U.S. Patent can be operated to blow air once every 5 times of pressing the patient's heart. Accordingly, the mouth and the nose of a rescuer are not necessary to contact the patient during the process of executing a first aid so as to prevent from any disease infection. The present inventor has made a lot of improvement regarding the device and a variety of functions disclosed in the present invention are not provided in said U.S. patent.

SUMMARY OF THE INVENTION

An object of the present invention is to provide an automatic blowing air device of cardiopulmonary resuscitation with which a constant force to press the heart can be maintained, an easy operation can be performed, a more oxygen can be obtained, and air blowing can be executed electrically and manually.

Another object of the present invention is to provide an automatic blowing air device of cardiopulmonary resuscitation, which is adjustable to adapted for the bust line of a patient swiftly and can be fixed at a correct position by sucking disks.

A further object of the present invention is to provide an automatic blowing air device of cardiopulmonary resuscitation, which can respond swiftly if the heart and the lung have a symptom of revival and can be available for supplying pure oxygen or fresh air while the heart beat is restored.

BRIEF DESCRIPTION OF THE DRAWINGS

The present invention can be more fully understood by referring to the following description and accompanying drawings, in which.

DETAILED DESCRIPTION OF THE PREFERRED EMBODIMENT

Figure 2:
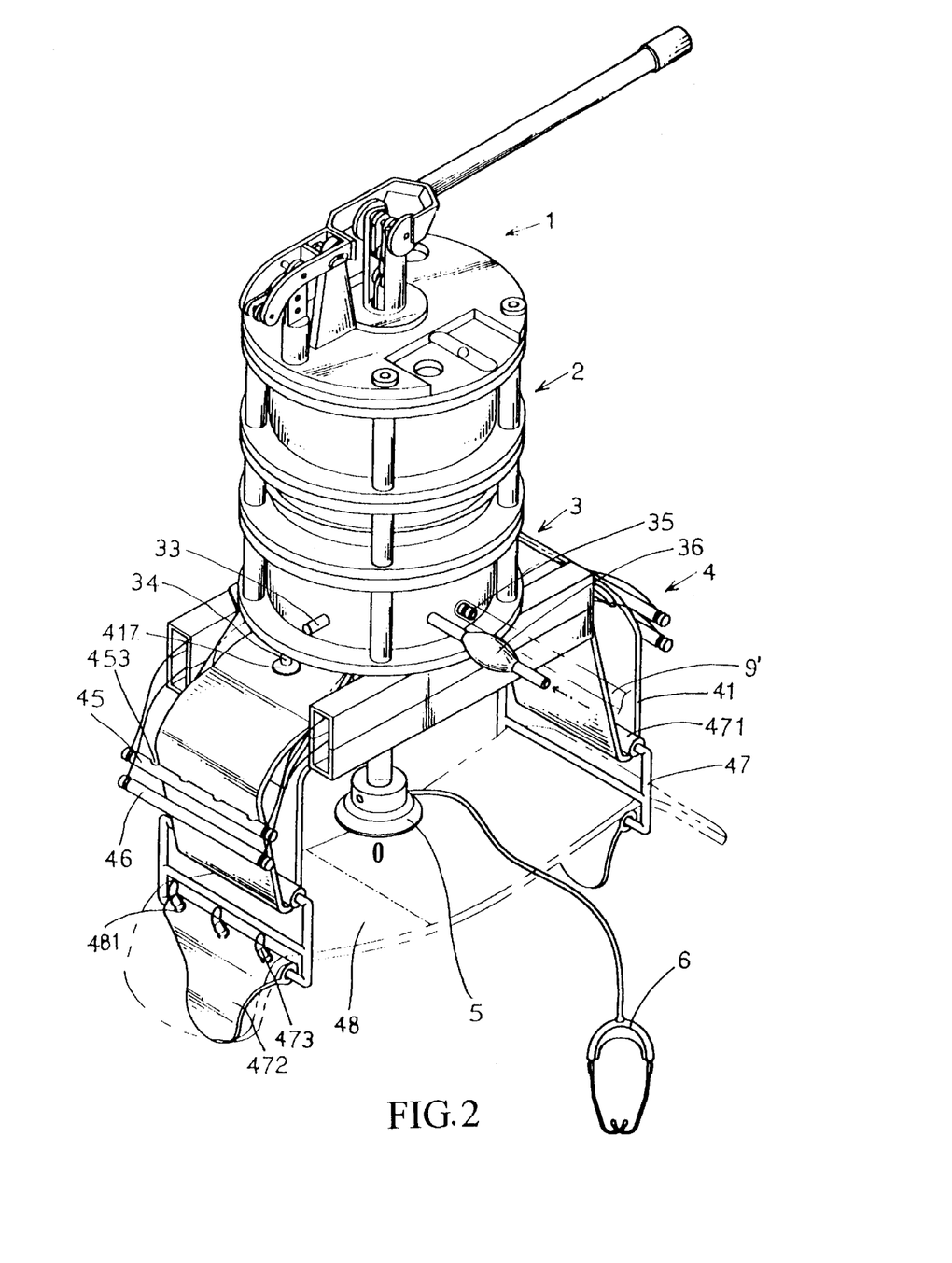
FIG. 2 is a perspective view of electric and manual pressing device of automatic air blowing for cardiopulmonary resuscitation in accordance with the present invention.

Referring to FIG. 2, the electrical and manual pressing device of automatic air blowing for first-aid cardiopulmonary resuscitation according to the present invention mainly comprises a press unit 1, a storage unit 2, control unit 3, a tying unit 4, a sucking disk 5 and a stethoscope 6.

Figure 3:
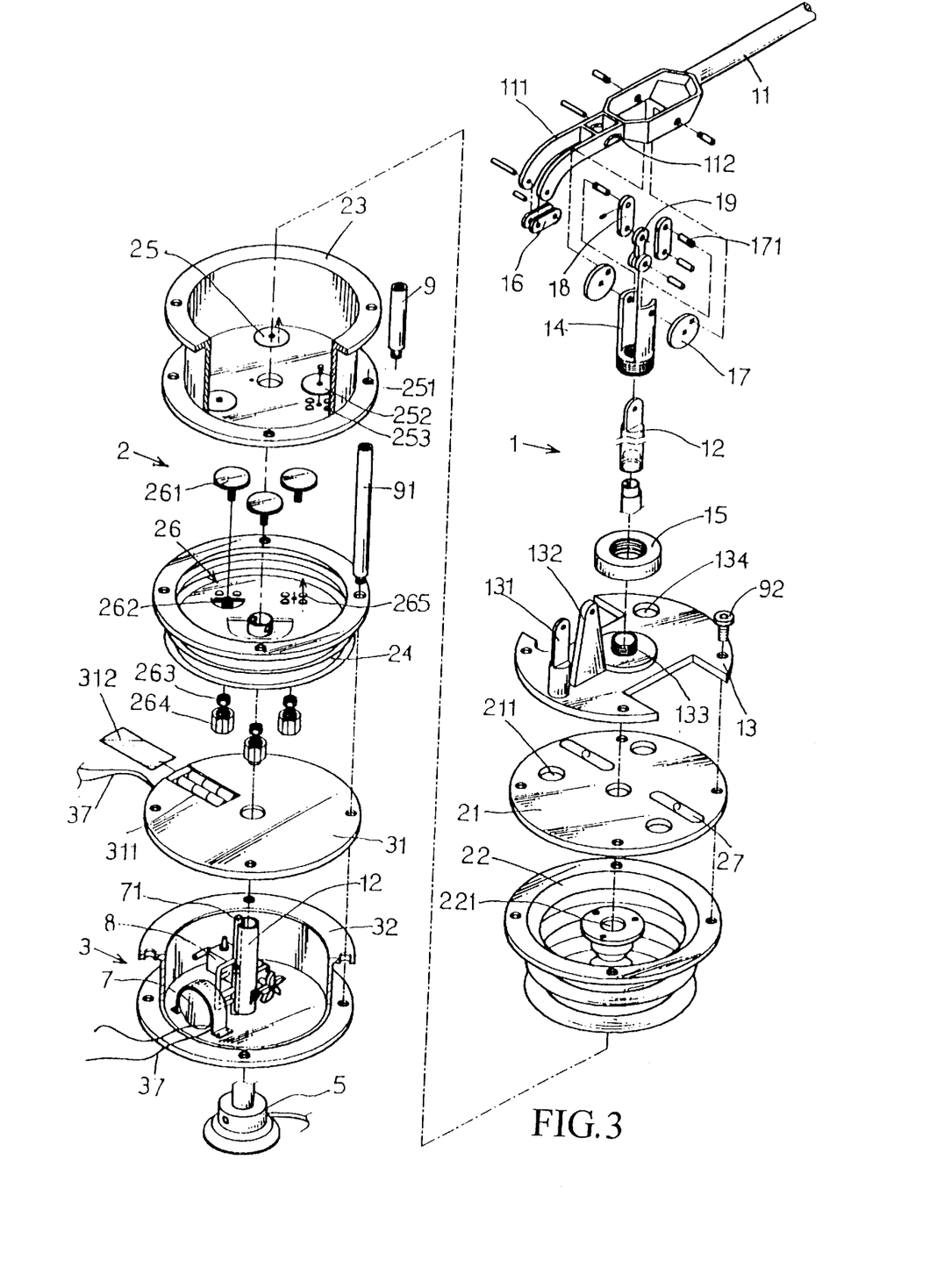
FIG. 3 is an exploded perspective view of a press unit, an air storage unit, and a control chamber unit in the device shown in FIG. 2.

Referring to FIG. 3, the press unit 1 further comprises a fixing plate 13 and a first upright bar 131 and a second upright bar 132 are attached on the plate 13. The fixing plate 13 has a central hole with a threaded cylinder 133 to engage with a support 14 and the support 14 has an threaded end to engage with a ring 15. A lever handle 11 at end thereof extends two arms 111 with free ends thereof being attached a first link 16 such that the first bar 131 can pivotally engage with said first link 16. An arc groove is provided on each of the arms 111 respectively to fit with locating pins at both side of the second bar 132. Said two arms 111 enclose and pivotally connect with two fly wheels 17 and a respective spindle 171 of the two fly wheels 17 each passes through said two arms respectively and pivotally connects a crank shaft 18 at both lateral sides thereof. The crank shaft 18 at a lower end thereof can be pivotally connected with a press head 12 at an upper end thereof via a second link 19. The lever handle 11 can actuate the press head 12 to maintain an up and down movement of equal stroke through the two flywheels 17, the crankshaft 18 and the second link 19. The air storage unit 2 comprises an air storage cylinder 23 and several first air valves 25 at a lower part thereof to allow the outside air entering into the cylinder 23 only. Each of said first air valves 25 is constituted by that a first air hole 253 at the bottom of the cylinder 23 is engaged with a first valve body 252 at an inner side of the first air hole 253 by first set screws 251. A flexible air pump 24 is located at the bottom of the air storage cylinder 23 to form an airtight engagement to each other. A second air valve 26 is located at a lower part of the flexible air pump 24 and comprises a screw bar of a second valve body 261 passing through a screw threaded cylinder 262 and engaging with a small nut 263. A big screw threaded cylinder 264 covers the small nut 263 and engages with the outer threaded surface of the cylinder 262 to allow the second valve body 261 fixing at the inner side of the second air opening 265. Said air storage cylinder 23 is provided with a resilient body 22 therein and the resilient body 22 at a top thereof engages with a top plate 21. The top plate 21 has a second air opening 211 to communicate with the first air opening 134 on the fixing plate 13. A central hole 221 in the resilient body 22 is an airtight engagement with the press head 12 and an airtight space is confined by an outer rim of the resilient body 22, an interior of the air storage cylinder 23 and the lower part of the top plate 21. Air levels 27 are attached on top of the top plate 21.

Referring to FIGS. 2 and 3 again, the control unit 3 comprises a receiving cylinder 32 to fix an air pump 7, an air pipe 71, and an air control valve 8 therein. A manual switch 33, a contact switch 34, an outlet head 35, and a pumping ball 36 are fixed at an outer surface of the cylinder 32. An upper cover 31 is on top of the cylinder 32 and the upper cover 31 has a battery box 311 thereon. A lid 312 is used to cover the battery box 311. Electric wires 37 are provided to connect the battery box 311, the air pump 7, the manual switch 33 and the contact switch 34. The outlet head 35 is connected with a mouth-nose breather via a communicating pipe (not shown), which is the same as the prior art shown in FIG. 1.

Figure 4:
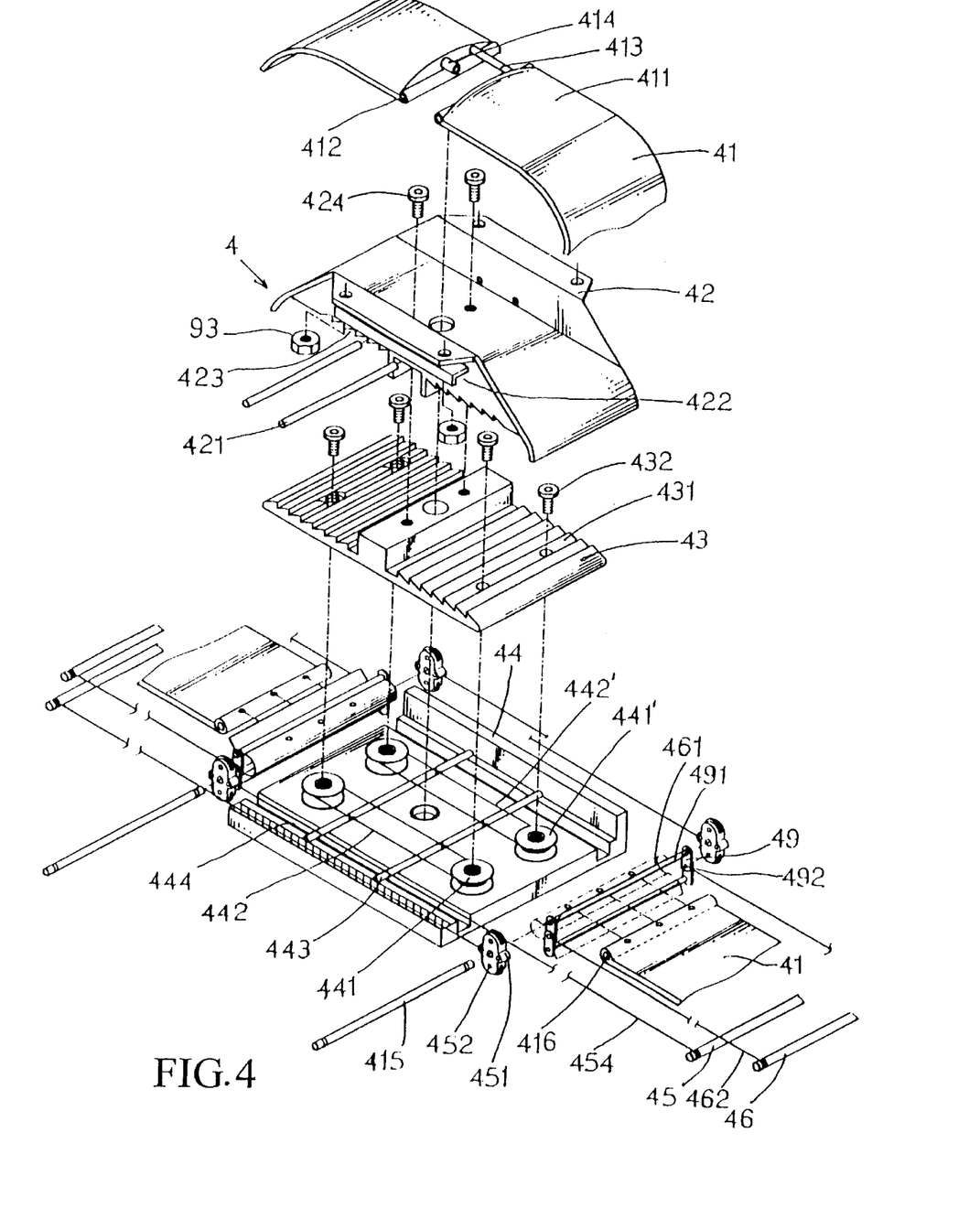
FIG. 4 is an exploded perspective view of part of a tying unit in the device shown in FIG. 2.

Referring to FIG. 4 and referencing FIG. 2 again, the tying unit 4 comprises multiple sets of identical apparatus, which are oppositely arranged at right and left sides. In order to simplify the description, one set of the apparatus is explained only. An upper band 41 at a top end thereof has an air bag 411 and the air bag 411 is fixed to an upper teeth plate 42 by way of a first pole 421 passing through a first hole 412. An air pipe 413 communicates air bags at both left and right sides and the air bag at the left side attaches a connector 414. The upper band 41 at a lower end thereof engages with a wheel assembly 451 and a leaf spring 461. The leaf spring 461 at both lateral sides thereof has a loose leaf 49 respectively to pivotally connect a press stick 491 for restricting an angular movement of the leaf spring 461. A base 44 pivotally engages with a first pulley set 441 and a second pulley set 441' and a first steel wire 442 and a second steel wire 442' enclose the first and the second pulley sets 441, 441' respectively. A third pole 443 engages with a lower hole 452 of the wheel assembly 451 and is positioned; across the first and second wires 442, 442' and fixes with the first and second wires 442, 442' respectively. The wheel assembly 451 moves along a lower groove rail 444 of the base 44 and an upper groove rail 422 of the teeth plate 42. A first pull bar 45 has a recess 453 to offer a better sense of hand touch and both ends of the first pull bar 45 are associated with another wheel assembly 451 via a first pull line 454. Both ends of a second pull bar 46 are associated with pivot holes 492 respectively on a loose leaf 49. A lower teeth plate 43 provided with lower teeth 431 is fastened to the base 44 by several screws 432. The upper teeth plate 42 at the bottom thereof is provided with upper engaging teeth 423 and fastened by set screws 424 directly above the lower teeth plate 43. An upper end and a lower end of the leaf spring 461 engage with the upper teeth 423 and the lower teeth 431 respectively. The upper band 41 at the middle section thereof engages with a roll 471 of the buckle 47 and the buckle 47 pivotally connects a engage part 472. The engage part 472 is provided with lock pins to engage with lock holes 481 on the lower band 48 such that the lower band 48 can be associated with the buckle 47. It can be seen in FIG. 5 that the lower band 48 has multiple rows of equally distant lock holes 481 and each row of lock holes 481 is marked an identified numeral at both side thereof.

Referring to FIG. 4 and referencing FIGS. 2 and 3 again, the fixing plate 13, the top plate 21, the resilient body 22, the air storage cylinder 23, the flexible air pump 24, the upper cover 31, the receiving cylinder 32, and the upper teeth plate 42 provide with through holes around the borders thereof respectively such that these through holes are aligned with each other to be passed through by upper threaded rods 9 and lower threaded rods 91 and be fastened by upper set screw 92 and lower nuts 93 respectively. In addition, the fixing plate 13, the top plate 21, the resilient body 22, the air storage cylinder 23, the flexible air pump 24, the upper cover 31, the receiving cylinder 32, and the upper teeth plate 42 have a aligned central hole respectively to be passed through by the press head 12. The press head 12 has an outer end thereof associated with the sucking disk 5 at an upper part thereof and the sucking disk 5 connects with a stethoscope 6.

Figure 5:
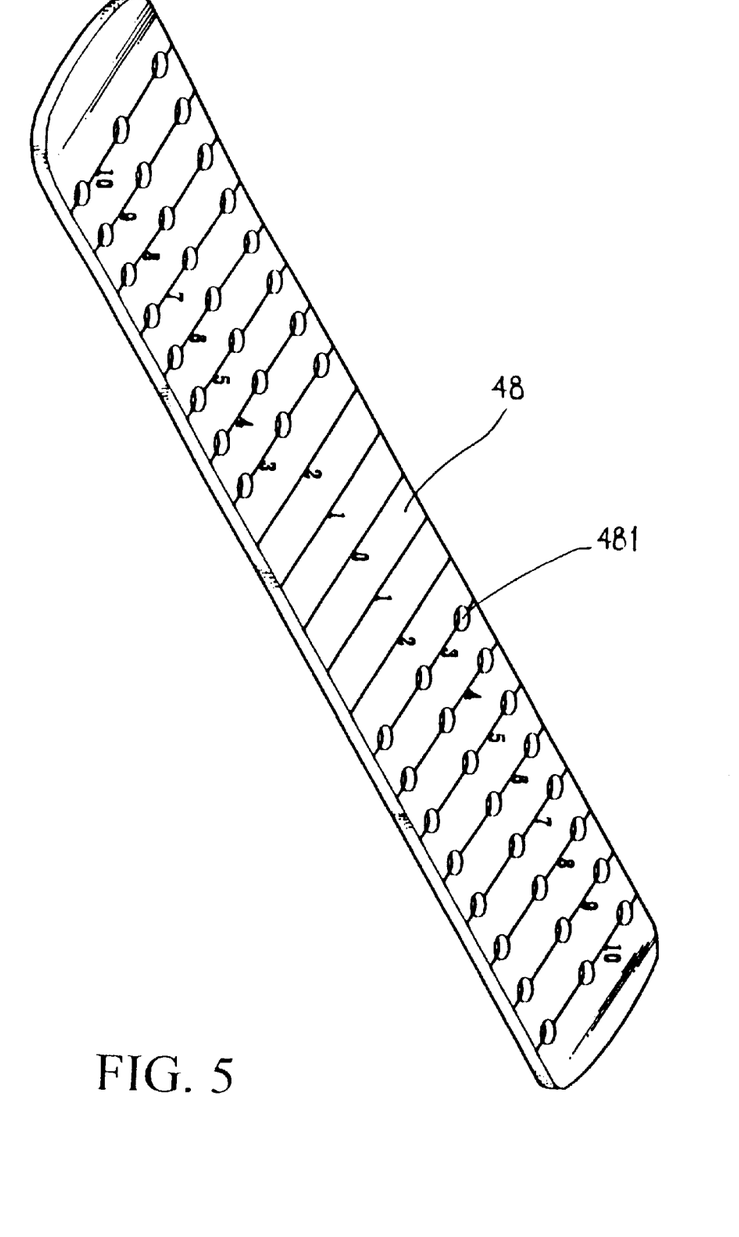
FIG. 5 is a perspective view of a lower band in the device shown in FIG. 2.

When the device according to the present invention is used, the lower band 48 is placed under a patient to align a central point of the patient's back with a central position 480 of the lower band 48. And, both ends of the lower band 48 pass through the buckle 47 respectively to allow buckle pins 473 passing through lock holes 481 marked with identical numerals. Moreover, a first pull bar 45 is located at both left and right lateral sides respectively and either one of the first pull bars can be pulled such that the length of the upper band 41 for tying the chest of the patient can be reduced simultaneously and equidistantly. In the meantime, a position of the upper band 41 at the bottom thereof can be fixed by way of the upper and the lower teeth 423, 431 and both ends of the leaf spring 461. In this way, the sucking disk 5 can be located at the correct position of the patient's heart quickly. Once the first-aid procedure is complete, either one of the second pull bars 46 at both left and right sides can be pulled to move the both sides of the loose leaf 49 toward the center thereof. Thus, the upper and the bottom surfaces of the leaf spring 461 can be separated from the restriction of both teeth 423, 431, and the lower part of the upper band may move outward to release the chest of the patient from tying.

Figure 6:
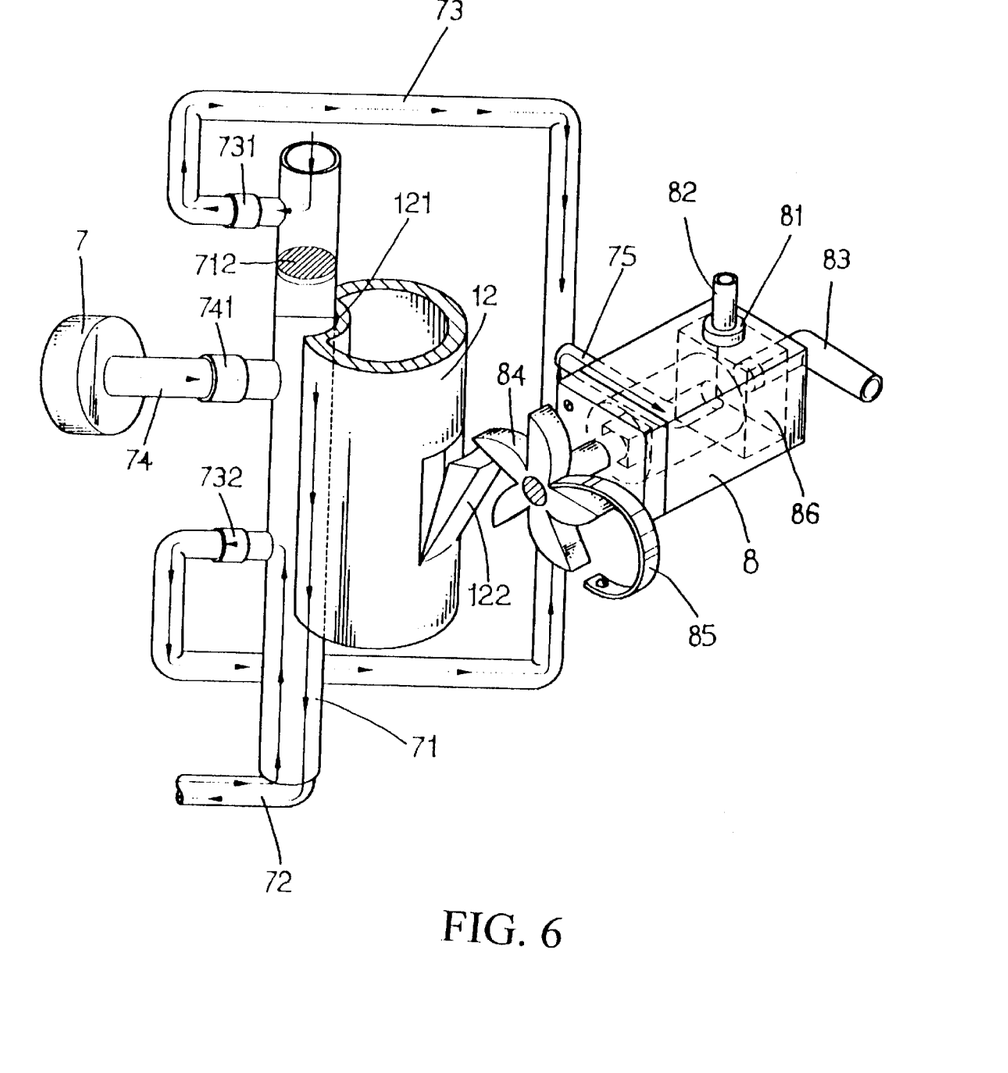
FIG. 6 is a perspective view of air flow passage adapted to the control unit in the device shown in FIG. 2.
Figure 10:
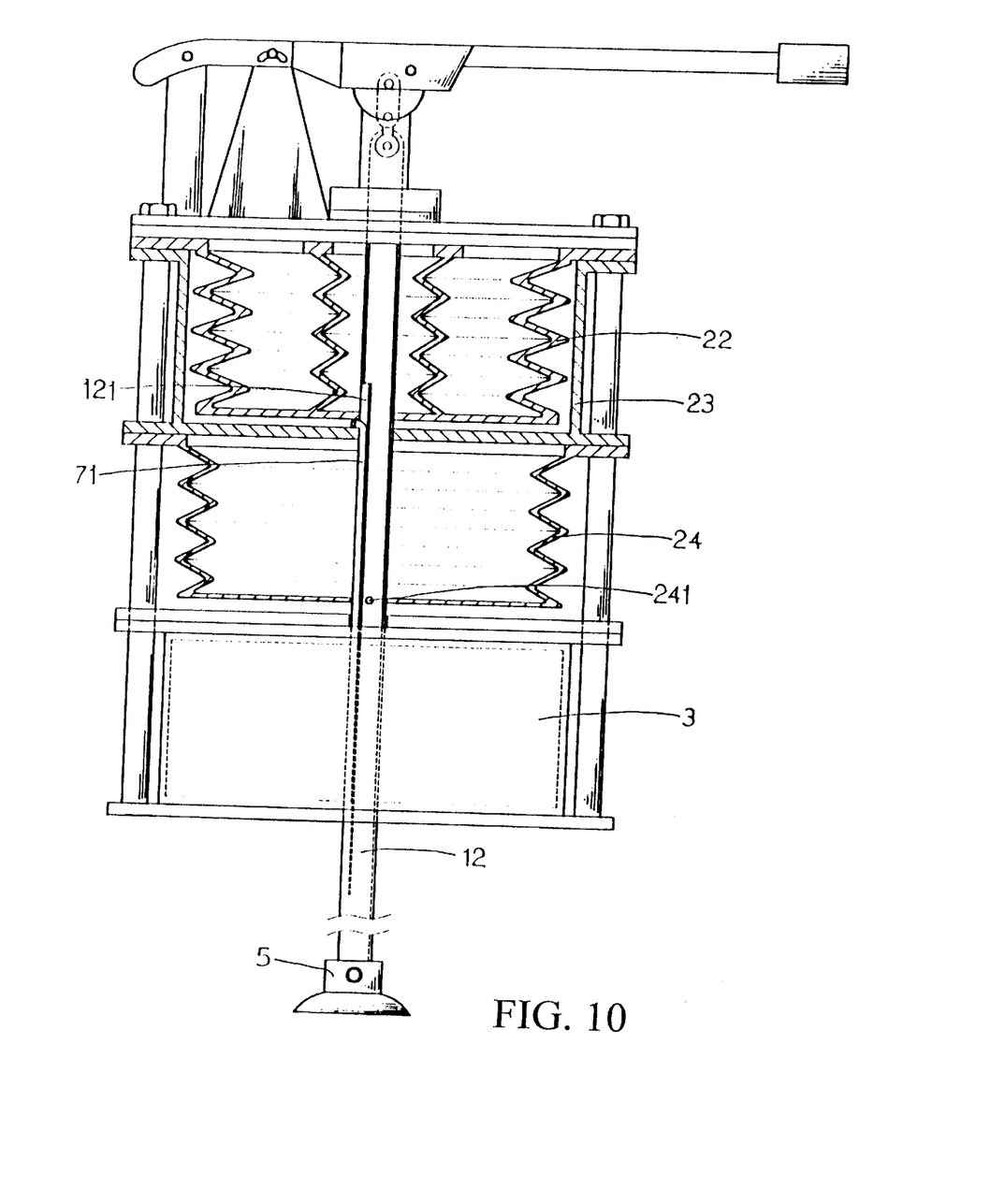
FIG. 10 is a sectional view of the air storage unit before air filling.

Referring to FIGS. 6 and 10 with accompanying with FIG. 3 again, the press head 12 has a recess part 121 to keep contact with an air pipe 71 made of hard material such that it prevents the press head 12 from rotation. The air pipe 71 has an opening at the upper end thereof extending to and fixing to a bottom of the air storage cylinder 23. A lower end of the air pipe 71 fixes to a bottom of the receiving cylinder 32 and communicates with a connector 414 at the upper band 41 via a first branch pipe 72. The air pipe 71 is divided into two sections, an upper section and a lower section, by a partition 712. The upper section of the air pipe 71 connects a second branch pipe 73 and the lower section of the air pipe 71 communicates the air pump 7 via a third branch pipe 74 and connects with the other end of the second branch pipe 73. The second branch pipe 73 further connects with a fourth branch pipe 75 to communicates the air control valve 8. The second and the third branch pipes 73, 74 are provided with a first, a second, and a third valves 731, 732, 741 respectively to limit the air in the pipes moving toward the air control valve 8 or the air pipe 71 only. The air control valve 8 connects with a fifth branch pipe 82 by way of an unidirectional guiding valve 81 to communicate with an outlet of the pumping ball 36 as shown in FIG. 2. An inlet of the pumping ball 36 is connected to a oxygen source (not shown in the figure). The air control valve 8 connects with a sixth branch pipe 83 to communicate with the air outlet 35. A lateral side of the air control valve 8 pivotally connects with a gear 84 and the gear 84 is resisted in a state of reversal by a lock band 85 and is rotated by way of a retaining piece 122 on the press head 12. When the retaining piece 122 pushes the gear 84 5 times, the air control valve 8 admits the air to enter from the fourth branch pipe 75 (it is a prior art disclosed in U.S. Pat. No. 5,823,185). In the meantime, the unidirectional guiding valve 81 prohibits the air to flow out of the fifth branch pipe 82 so as to enter the mixing chamber 86 for combining the oxygen coming from the unidirectional guiding valve 81. The mixture of the air and the oxygen then flows toward the mouth-nose breather 8' through the sixth branch pipe 83, the air outlet 35, and the air passage 9' shown in FIG. 1 to offer the patient blowing air.

Figure 7:
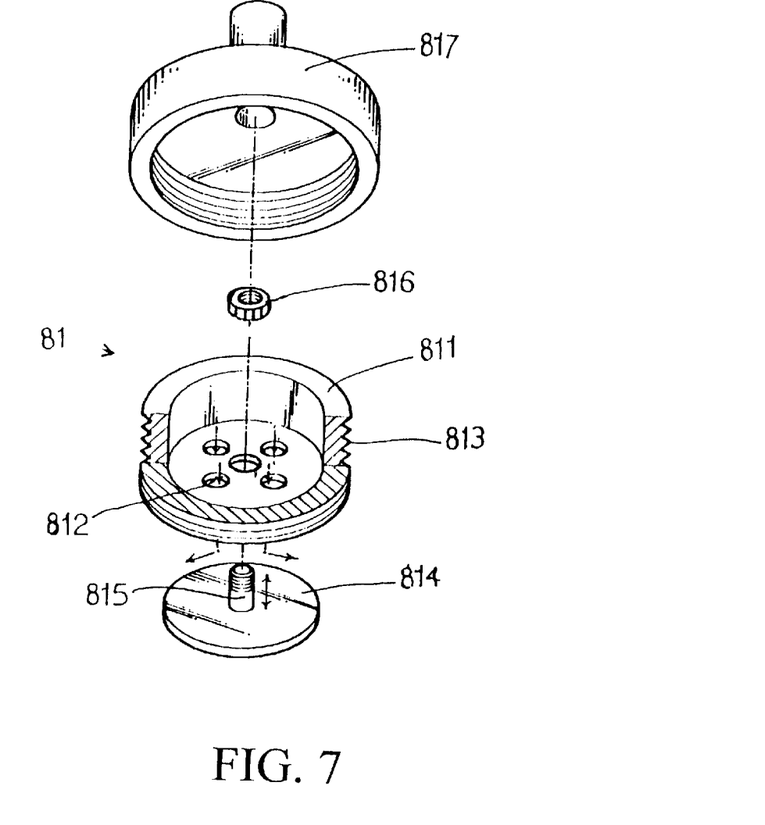
FIG. 7 is an exploded perspective view of an unidirectional guiding valve in the device shown in FIG. 2.

Referring to FIG. 7, the unidirectional guiding valve 81 comprises a main body 811 with air openings 812 and a central hole at a bottom thereof respectively. The main body 811 has external screw threads 813 thereon and is passed through by a screw stem 815 attached on a valve disk 814. The screw stem 815 engages with a nut 816 and a cap 817 engages with and covers the main body 811 at the external screw threads 813 thereof.

Figure 8:
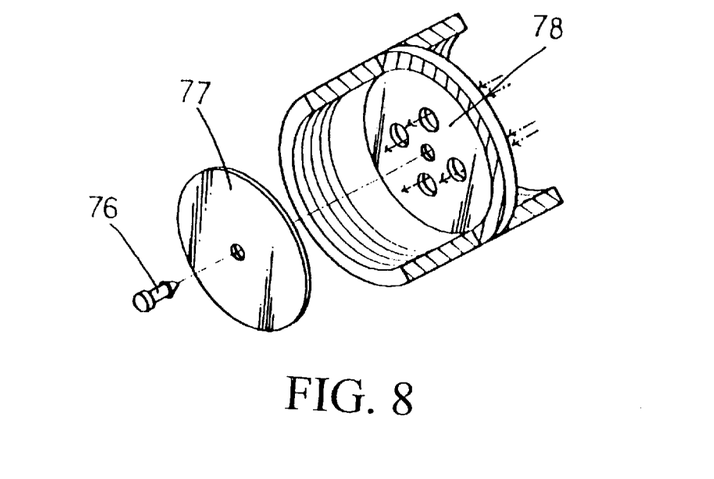
FIG. 8 is an exploded perspective view of a valve in the device shown in FIG. 2.

Referring to FIG. 8, each of the first, the second, and the third valves 731, 732, 741 comprises a set screw 76 to engage a valve disk 77 with a valve wall 78.

Figure 9:
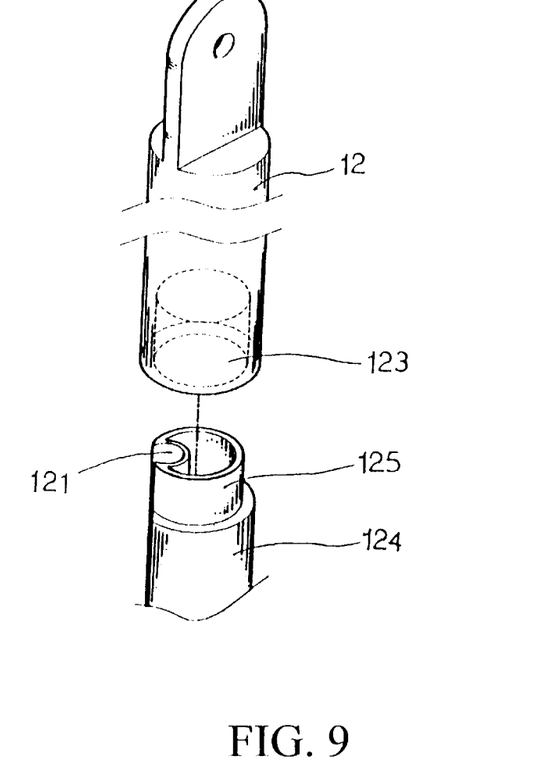
FIG. 9 is a fragmentary perspective view of a press bar showing an engaging hole and a sleeve part thereof.

Referring to FIG. 9 and referencing FIG. 10 again, the recess 121 provided on the press head 12 is between approximate 6 centimeters below the bottom of the control unit 3 and approximate 6 centimeters above the bottom of the air storage cylinder 23 for receiving the air pipe 71. The press head 12 has an upper portion provided with an engaging hole 123 to fix to an engaging part 125 on an upper end of the recess section 124.

Figure 11:
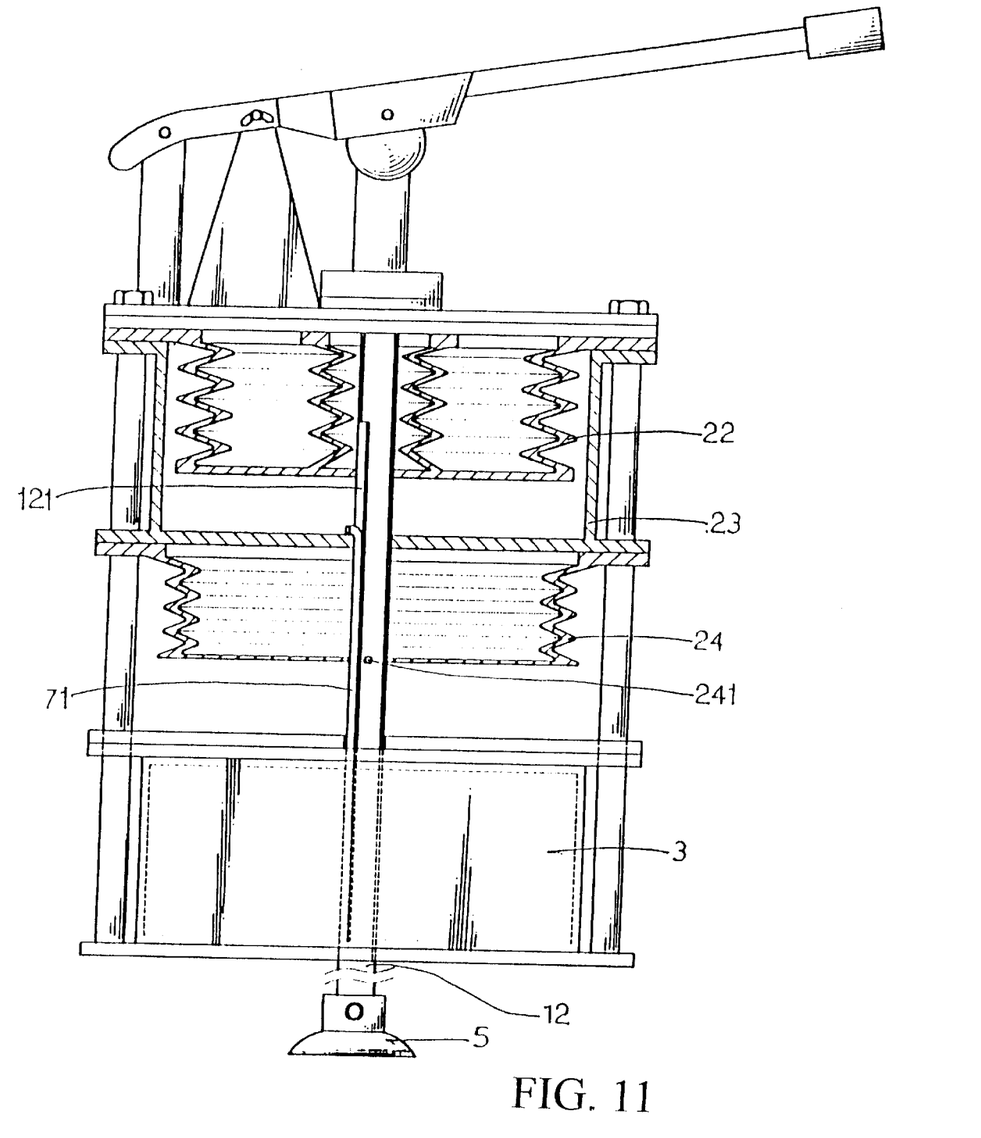
FIG. 11 is a sectional view of the air storage unit in a state of partly air filling.

Referring to FIGS. 3 and 10 again, the flexible air pump 24 at a bottom thereof is engaged with the press head 12 by using set screws 241. When the manual mode is operated to blow air, the flexible air pump 24 admits the air through the second air valve 26 accompanying with the sucking disk 5 being actuated to press the patient' heart at the moment of pressing down the press head. And, the second air valve 26 is shut and the air enters the air storage cylinder 23 at the moment of raising the press head 12. As shown in FIG. 11, the bottom of the resilient body 22 will be pushed upward in the process of the air entering the air storage cylinder 23. When the press head 12 is raised at the fifth time, a maximum air is filled in the air storage cylinder 23 and the bottom of the resilient body 22 rises at the highest position. Under this circumstance, the air control valve 8 is actuated to allow the fourth branch pipe 75 communicating with the air mixing chamber 86 and the air in the flexible air pump 24 is pushed by the press head 12. Moreover, the air in the air storage cylinder 23 can be pushed by the resilient body 22 to move toward the mouth-nose breather for the patient to blow the air. Again, the air enters the resilient body 22 through the first and the second air openings 134, 211 and the bottom of the resilient body 22 moves back to the lowest position. It is noted that press head 12 in the device of the present invention is raised and the air can fills in the air storage cylinder 23 such that a constant press force against can be maintained without change. But, it can be understood that the device disclosed in U.S. Pat. No. 5,823,185 provides that air filling is executed in the process of the pressing shaft 1' and the more times are pressed the greater forces are required. And, it is disadvantageous that the force to press the heart is getting larger.

In case of electrical mode of air blowing, the first air valve 26 at the bottom of the flexible air pump 24 is adjusted to move the big threaded cylinder 264 upward so as to contact the small nut 263 as shown in FIG. 3. In this way, the second valve disk maintains in a state of opening to enable the air in a two-way communication such that the air in the flexible air pump 24 will not enter the air storage cylinder 23 at the time of raising the press head 12. The press head 12 only performs the functions of pressing the heart and moving the gear 84 on the air control valve 8. When the manual switch 33 is opened, the air is transmitted by the air pump 7 to the air bag 411 shown in FIG. 4 via the first branch pipe 72 at lower section of the air pipe 71 shown in FIG. 6. When the air bag 411 is full with the air as shown in FIG. 2, the hard board 417 moves up to turn on the contact switch 34 and the air pump 7 stops to fill the air. When the press head is pressed five times to communicate the air control valve 8 with the fourth branch pipe 75 and the mixing chamber 86, the air in the air bag 411 can be sent to the mouth-nose breather through the air control valve 8 and etc.

The arrangement related to the air filling of the manual pressing and of the electric actuating can be assembled independently and operated alone. If the mechanism of the manual pressing is applied only, the mechanism of the electric actuation is not necessary to set up in the device. Contrarily, if the mechanism of the electric actuation is adopted, the mechanism of the manual pressing is not necessary to set up. Thus, a considerable production cost can be saved substantially.

Figure 12:
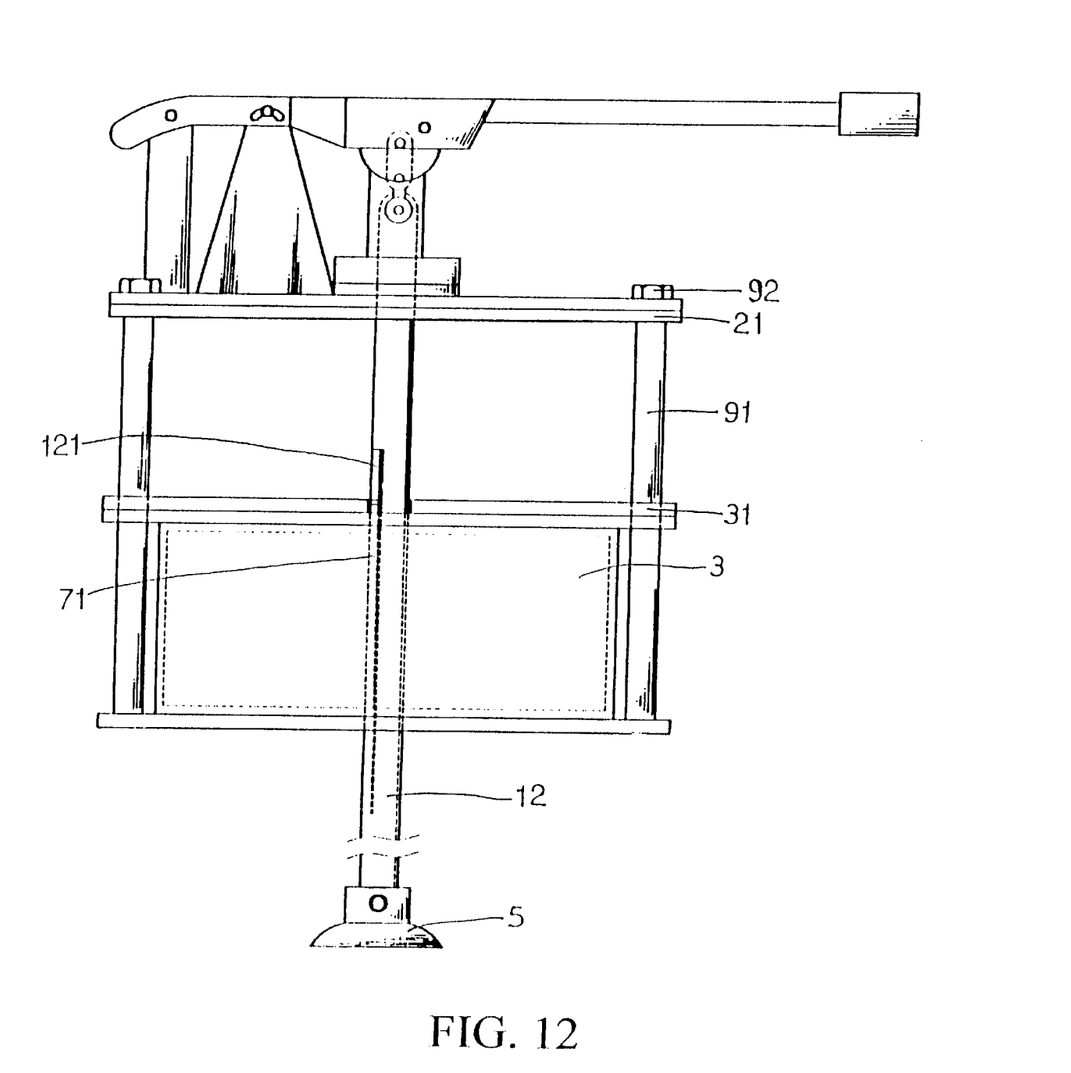
FIG. 12 is a sectional view of the press unit and the control unit in another preferred embodiment thereof.

Referring to FIG. 12, another preferred embodiment is illustrated to show an electric blowing air device of first-aid cardiopulmonary resuscitation. Comparing to the first preferred embodiment shown in FIGS. 2 and 3, the upper threaded rod 9 and the air storage unit 2 in the first embodiment is not provided in the electric blowing device. And, the top plate 21 remains unchanged and the upper screws 92 engages with the lower threaded rod 91 such that the air pipe 71 can be fixed beneath the upper cover 31. The operation of the present embodiment is the same as that of the electric mode in the preceding description. Therefore, it is appreciated that the present embodiment can perform functions of electrically blowing air and pressing the heart.

Figure 13:
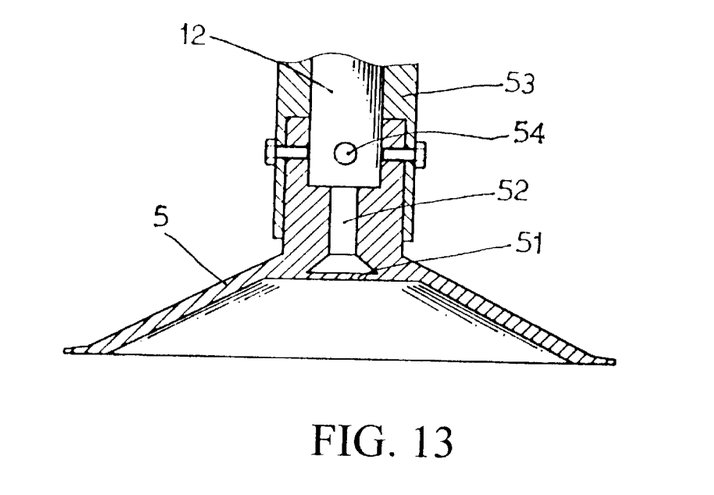
FIG. 13 is a sectional view of a sucking disk in the device shown in FIG. 2.

Referring to FIG. 13, the sucking disk 5 is provided with a diaphragm 51 and a hollow part 52 therein. An end of the sucking disk 5 fits and engages with the lower end of the press head 12 by way of a sleeve ring 53. The press head 12 at the lower end thereof has a passage to communicate with the hollow part 52. The sleeve ring is provided with a fitting hole 54 for connecting with the stethoscope and communicates the passage.

The electrical and manual pressing device of automatic air blowing for first-aid cardiopulmonary resuscitation according to the present invention has functions without providing in the device of U.S. Pat. No. 5,823,185 such as filling the air by way of electrical actuation or manual pressing, offering a great deal of air, maintaining a constant pressing force against the heart, quickly fixing the sucking disk at a proper pressing position based on the size of the patient' body, quickly checking a breathing reaction of the patient by way of the air level, checking the heart beat by way of the stethoscope, mixing the oxygen with the air through the air mixing chamber in the air control valve, supplementing the oxygen or the fresh air after the heat beat restoring by way of the pumping ball, and etc. In addition, the entire construct of the device in accordance with the present invention has many novel arrangements, which are not disclosed in the device of U.S. Pat. No. 5,823,185.

While the present invention has been described with reference to preferred embodiments thereof, it is to be understood that modifications and variations may be easily made without departing from the spirit of this invention, which is defined by the appended claim.

What is claimed is:

1. An electrical and manual pressing device of automatic air blowing for first-aid cardiopulmonary resuscitation, comprising:

a) a press unit including:

a fixing plate with a central through hole and a plurality of air holes, the fixing plate having a first bar, and a support around a central hole;

a lever handle with two extending arms at an end, said two arms having free ends attached to a first link, said first link pivotally engaging the first bar;

two fly wheels located on said two arms, a spindle passing through said two arms respectively; and two crank shafts, each of said crank shafts having first and second ends, said first ends pivotally connecting with said spindle; and a press head with first and second ends, the first end pivotally connecting with the second ends of said crank shafts via a second link, and including a retaining piece with a recess section thereon respectively;

b) a storage unit including:

an air storage cylinder with a top and a bottom, and being provided with a resilient body, said top engaging a top plate thereon, said top plate at a lower edge thereof fixing said resilient body at an upper edge thereof, said top plate having an air opening in communication with said air holes on the fixing plate and said resilient body, said bottom having a first air valve for admitting air;

a flexible air pump with a bottom part, and being in airtight engagement with the bottom of said air storage cylinder, said bottom part having a second air valve, and fixedly connecting with said press head;

c) a control unit placed below said flexible air pump, and including:

a receiving cylinder with a bottom;

an air pipe with two ends, the air pipe being made of hard material and disposed in said receiving cylinder in contact with the recess section on said press head, one of the two ends extending into said air storage cylinder and fixed to said air storage cylinder at the bottom thereof, the other one of the two ends fixed to the bottom of the receiving cylinder;

an air control valve disposed in said receiving cylinder, and communicating with said air pipe via a first branch pipe;

an outlet head disposed on said receiving cylinder, and communicating with said air control valve via a second branch pipe; and a gear located aside said air control valve and pivotally connecting with said air control valve, the gear resisting a reverse rotation by a lock band and rotated forward by way of the retaining piece on said press head;

d) a tying unit located under said control unit;

e) a sucking disk, engaging with the second end of said press head and adapted to be pressed against a patient's heart;

f) an air passage pipe with first and second ends, the first end connecting with an outlet; and g) a mouth-nose breather, connected to the second end of said air passage pipe;

wherein, said fixing plate, said top plate, said resilient body, said air storage cylinder, said flexible air pump, said receiving cylinder, and said tying unit have through holes at a lateral side thereof respectively engaged by a plurality of threaded rods and fastened by screws and nuts, and with a central hole respectively to be passed by said press head.

2. The electrical and manual pressing device of automatic air blowing for first-aid cardiopulmonary resuscitation as defined in claim 1, wherein said tying unit further comprises a base, having a pair of first side groove rails, pivotally engaging a first pulley set and a second pulley set respectively;

an upper teeth plate, with first teeth thereon, having a pair of second side groove rails, having through holes at lateral sides thereof to accommodate the plurality of threaded rods, and having a central through hole for accommodating the press head, and being located above said base;

a lower teeth plate, with second teeth opposite to the first teeth on said upper teeth plate, and having a central hole for accommodating the press head, and being disposed on said base;

two upper bands with ends respectively, being oppositely arranged and engaging with each other, and engaging said upper teeth plate at a top thereof;

two leaf springs, with two ends respectively, each of said leaf springs engaging said upper bands at said ends respectively, at both lateral sides thereof having a loose leaf pivotally connecting a press stick for restricting an angular movement of the leaf spring, and both ends thereof connected with the teeth of said upper and said lower teeth plates respectively;

a first steel wire and a second steel wire, enclosing the first and the second pulley sets respectively;

two wheel assemblies, engaging said upper bands at said ends respectively, and moving along said pairs of first and second side groove rails respectively;

two poles positioned across and fixed to the first and second steel wires respectively, and pivotally connecting said two wheel assemblies;

a first pull bar with two ends, each end thereof being associated with one of said two wheel assemblies;

a second pull bar with two ends, the ends thereof being associated with pivot holes respectively on said loose leaf; and two buckles, each of the buckles engaging with the upper bands at middle sections thereof respectively, and having an engage part with lock pins.

3. The electrical and manual pressing device of automatic air blowing for first-aid cardiopulmonary resuscitation as defined in claim 2, wherein said second air valve comprises a screw bar in a second valve body passing through a screw threaded cylinder and engaging a nut, a screw threaded cylinder covering the nut and engaging an outer threaded surface of the screw threaded cylinder; the receiving cylinder engages an air pump, and includes a manual switch, and a contact switch fixed to an outer surrounded surface of the receiving cylinder, an upper cover located on top of the receiving cylinder and the upper cover has a battery box thereon, a lid covering the battery box, electric wires connecting the battery box, the air pump, the manual switch and the contact switch; said two upper bands at top ends thereof each have an air bag, an air pipe communicating with the air bags, said air pipe at a lower end thereof communicating with a connector at the upper band via a first branch pipe, and is divided into an upper section and a lower section by a partition, the upper section of the air pipe connected to a second branch pipe and the lower section of the air pipe communicates with the air pump via a third branch pipe and is connected to the second branch pipe, the second branch pipe further connected to a fourth branch pipe in communication with the air control valve, the second and the third branch pipes are provided with first, second, and third valves respectively to limit air in the pipes from moving toward the air control valve and the air pipe.

4. The electrical and manual pressing device of automatic air blowing for first-aid cardiopulmonary resuscitation as defined in claim 3, wherein the receiving cylinder at the outer surface thereof engages a pumping ball; the air control valve communicates with a fifth branch pipe via a unidirectional guiding valve to connect an outlet head of the pumping ball; the air control valve has a mixing chamber therein connecting with the unidirectional guiding valve and a sixth branch pipe communicates with the outlet head; the unidirectional guiding valve comprises a main body with air openings at a bottom thereof, the main body having external screw threads thereon and has a screw stem attached on a valve disk and engaging a nut, and a cap engages with and covers the main body at the external screw threads thereof.

5. The electrical and manual pressing device of automatic air blowing for first-aid cardiopulmonary resuscitation as defined in claim 4, wherein said top plate provides air levels thereon.

6. The electrical and manual pressing device of automatic air blowing for first-aid cardiopulmonary resuscitation as defined in claim 5, wherein the sucking disk has a diaphragm and a hollow portion therein, an end of the sucking disk engaging the lower end of the press head by way of a sleeve ring, the press head at the lower end thereof has a passage communicating with the hollow portion, the sleeve ring provided with a fitting hole for connecting with a stethoscope and which communicates with the passage.

7. The electrical and manual pressing device of automatic air blowing for first-aid cardiopulmonary resuscitation as defined in claim 6, wherein said fixing plate has a second upright bar, an arc groove is provided on each of the arms respectively engaging locating pins at both side of the second bar, and each row of lock holes on said lower band is marked an identified numeral.

8. An electrical device of automatic air blowing for first-aid cardiopulmonary resuscitation, comprising:
 a) a press unit including:
  a fixing plate with a central through holes and air holes, the fixing plate having a first bar, and a support around a central hole;
  a lever handle with two extending arms at an end, said two arms having free ends attached to a first link which is pivotally engaged with the first bar;
  two fly wheels located on said two arms, a spindle passing through said two arms respectively, and
  two crank shafts, each of said crank shafts having first and second ends, said first ends pivotally connecting with said spindle;
  a press head with first and second ends, the first end pivotally connecting with the second ends of said crank shafts via a second link, and including a retaining piece with a recess section thereon respectively; and
  a top plate located under said fixing plate and connected therewith;
 b) a control unit, placed below said top plate, and including:
  a receiving cylinder with a bottom, an air pipe and an air control valve mounted therein respectively, and an outlet thereon;
  an upper cover, attached to the receiving cylinder at top thereof, having a battery box thereon covered by a lid;
  an air pipe made of hard material, having a first closed end attached to said upper cover, and a second end mounted to the bottom of said receiving cylinder, and contacting the recess section on said press head;
  an air control valve disposed in said receiving cylinder, and communicating with said air pipe by way of a first branch pipe;
  an air pump disposed in said receiving cylinder and electrically connected to said battery box;
  an air outlet disposed on said receiving cylinder, and communicating with said air control valve by way of a second branch pipe;
  a manual switch disposed on said receiving cylinder, and electrically connected to said battery box;
  a contact switch disposed on said receiving cylinder, and electrically connected to said battery box;
  a gear located aside said air control valve and pivotally connecting with said air control valve, the gear resisting reversal by a lock band and rotated forward by way of the retaining piece on said press head;
 c) a tying unit located under said control unit and including:
  a base, having a pair of first side groove rails, pivotally engaging a first pulley set and a second pulley set respectively;
  an upper teeth plate, with first teeth thereon, having a pair of second side groove rails, having through holes at lateral sides thereof to accommodate the threaded rods, and having a central through hole for accommodating the press head, and being located above said base;
  a lower teeth plate, with second teeth opposite to the teeth on said upper teeth plate, and having a central hole accommodating the press head, and being disposed on said base;
  two upper bands with ends respectively, being oppositely arranged and engaging with each other, and engaging said upper teeth plate at a top thereof, the upper bands each including an air bag respectively, an air pipe communicating with the air bags, said air pipe at a lower end thereof, communicating with a connector at the upper bands via a first branch pipe, and being divided into an upper section and a lower section, by a partition, the upper section of the air pipe connected to a second branch pipe and the lower section of the air pipe communicating with the air pump via a third branch pipe and is connected to the second branch pipe, the second branch pipe further connected to a fourth branch pipe in communication with the air control valve, the second and the third branch pipes including first, second, and third valves respectively to limit air in the pipes from moving toward the air control valve and the air pipe;
  two leaf springs with two ends respectively, each of the leaf springs engaging said upper bands at said ends respectively, at both lateral sides thereof having a loose leaf pivotally connecting a press stick for restricting an angular movement of the leaf spring, and both ends thereof connected with the teeth of said upper and said lower teeth plates respectively;
  a first steel wire and a second steel wire, enclosing the first and the second pulley sets respectively;
  two wheel assemblies, engaging said upper bands at said ends respectively, and moving along said pairs of first and second side groove rails respectively;

two poles positioned across and fixed to the first and second wires respectively, and pivotally connecting said two wheel assemblies;

a first pull bar with two ends, each end thereof being associated with one of said two wheel assemblies;

a second pull bar with two ends, the ends thereof being associated with pivot holes respectively on said loose leaf; and two buckles, each of the buckles engaging with the upper bands at middle sections thereof respectively, and having an engage part with lock pins respectively;

d) a sucking disk engaging with the second end of said press and adapted to be pressed against a heart of a patient;

e) an air passage pipe with first and second ends, the first end connecting with said outlet; and f) a mouth-nose breather, connected to the second end of said air passage pipe and communicating with said air outlet;

wherein, said fixing plate, said top plate, said receiving cylinder, and the upper teeth plate have through holes at a lateral side thereof respectively engaged by a plurality of threaded rods and fastened by screws and nuts, and with a central hole respectively to be passed by said press head.

9. The electrical device of automatic air blowing for first-aid cardiopulmonary resuscitation as defined in claim 8, wherein the receiving cylinder at the outer surface thereof engages a pumping ball; the air control valve communicates with a fifth branch pipe via a unidirectional guiding valve to connect an outlet head of the pumping ball; the air control valve has a mixing chamber therein connecting with the unidirectional guiding valve and a sixth branch pipe communicates with the outlet head; the unidirectional guiding valve comprises a main body with air openings at a bottom thereof, the main body having external screw threads thereon and has a screw stem attached on a valve disk and engaging a nut, and a cap engages with and covers the main body at the external screw threads thereof.

10. The electrical device of automatic air blowing for first-aid cardiopulmonary resuscitation as defined in claim 9, wherein said top plate provides air levels thereon.

11. The electrical device of automatic air blowing for first-aid cardiopulmonary resuscitation as defined in claim 10, wherein the sucking disk has a diaphragm and a hollow portion therein, an end of the sucking disk engaging the lower end of the press head by way of a sleeve ring, the press head at the lower end thereof has a passage communicating with the hollow portion, and the sleeve ring provided with a fitting hole for connecting with a stethoscope and which communicates with the passage.

12. The electrical device of automatic air blowing for first-aid cardiopulmonary resuscitation as defined in claim 11, wherein said fixing plate has a second upright bar, an arc groove is provided on each of the arms respectively engaging locating pins at both sides of the second bar, and each row of lock holes on said lower band is marked an identified numeral.

* * * * *